United States Patent [19]

Hill

[11] Patent Number: 5,623,017
[45] Date of Patent: Apr. 22, 1997

[54] CLEAR SILICONE GELS

[75] Inventor: Randal M. Hill, Midland, Mich.

[73] Assignee: Dow Corning Corporation, Midland, Mich.

[21] Appl. No.: 598,451

[22] Filed: Feb. 8, 1996

[51] Int. Cl.$^6$ .................................................. C08K 3/20
[52] U.S. Cl. ........................... 524/860; 524/837; 424/401
[58] Field of Search .................................. 524/860, 837; 424/401

[56] References Cited

U.S. PATENT DOCUMENTS

| | | | |
|---|---|---|---|
| 3,299,112 | 1/1967 | Bailey | 260/448 |
| 4,999,398 | 3/1991 | Graiver | 524/837 |
| 5,486,566 | 1/1996 | Katsoulis | 524/773 |

OTHER PUBLICATIONS

"Microemulsions Theory & Practice", Leon M. Prince, Academic Press, pp. 7–10, (1977).

Primary Examiner—Margaret W. Glass
Attorney, Agent, or Firm—James L. DeCesare

[57] ABSTRACT

A method of forming a thermodynamically stable transparent product by combining (i) water; (ii) a volatile cyclic methyl siloxane or volatile linear methyl siloxane; and (iii) a silicone polyether surfactant. The amounts of each component, the particular type of silicone polyether surfactant used, and the order of addition of the components, influence the type of product obtained, and these factors are such that the composition forms an optically clear gel. The gel is useful in personal care products such as cosmetics and antiperspirants.

7 Claims, 1 Drawing Sheet

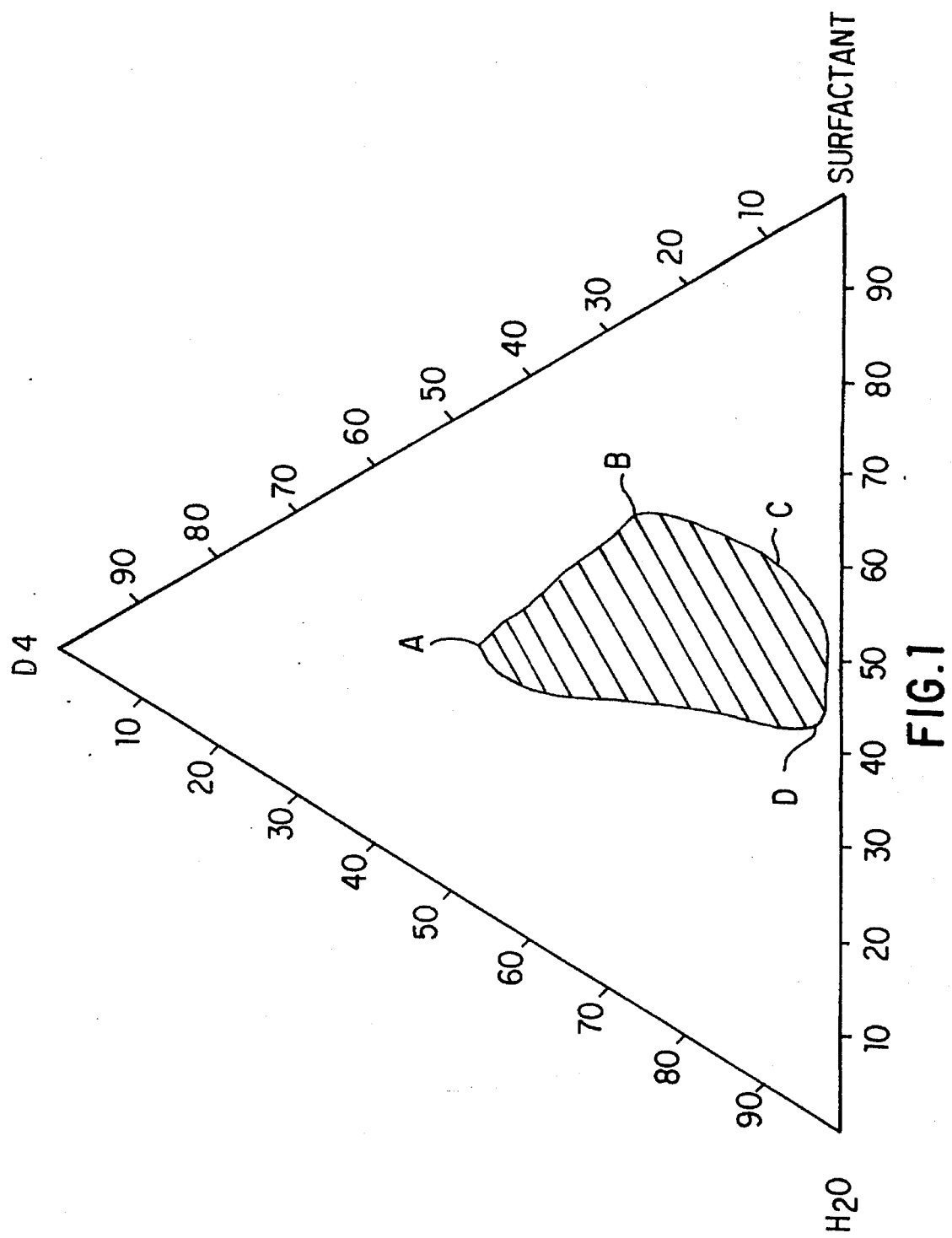

CLEAR SILICONE GELS

CROSS-REFERENCE TO RELATED APPLICATIONS

This application is related to my prior copending U.S. application Ser. No. 08/560,561, filed Nov. 20, 1995, entitled "Spontaneously Formed Clear Silicone Microemulsions", assigned to the same assignee as the present application. In the prior application I describe a ternary system that forms a microemulsion, whereas in the present application a ternary system forms a gel.

BACKGROUND OF THE INVENTION

This invention is directed to a transparent silicone, and more particularly to a ternary composition of water, a volatile cyclic or linear methyl siloxane (VMS), and a short-chain or low molecular weight silicone polyether, which when combined provide an optically clear gel.

It is well documented (i.e.; U.S. Pat. No. 4,999,398) that emulsions, especially silicone emulsions, are opaque, cloudy, and tend to separate on standing. Thus, the desirability of microemulsions which contain micro-particles in the droplet phase providing a measure of clarity, or gels which are thermodynamically stable transparent structures.

As used herein, the term emulsion or macroemulsion means a dispersion of one immiscible liquid in another, in the form of droplets with diameters approximately in the range of 100–1,000 nanometers (0.1–1.0 microns/1,000–10,000 angstroms Å).

In contrast, a microemulsion means a transparent dispersion of two or more immiscible liquids and a surfactant. Microemulsions are clear or transparent because they contain particles smaller than the wavelength of visible light, which is typically on order of about 10–100 nanometers.

Microemulsions may contain oil droplets dispersed in water (O/W), water droplets dispersed in oil (W/O), or they may be in the form of a bi-continuous structure. They are characterized by an ultra-low interfacial tension between the oil and water phases.

A microemulsion can be recognized by several of its inherent characteristics which are that (i) it contains oil, water, and a surfactant; (ii) there is a high concentration of surfactant relative to oil; (iii) the system is optically clear; (iv) the phases do not separate by centrifugation; and (v) the system forms spontaneously.

Thus, as used herein, an emulsion is considered as containing particles having an average diameter of more than 100 nanometers (0.1 microns/1,000 angstroms Å), whereas a microemulsion is considered as containing particles having an average diameter of less than 100 nanometers (0.1 microns/1,000 angstroms Å).

Clarity or transparency is controlled to a great extent by the particle size of the dispersed phase. The scattering of light is dependent on the particle size. Therefore, clear or transparent compositions appear to be a single phase without droplets or particles when viewed with the naked eye.

On the other hand, and in contrast to an emulsion or microemulsion, a gel is a semi-solid stabilized or set by a three-dimensional lattice system. Because a surfactant has a bipolar amphiphilic structure (i.e., a water-soluble polar head and a water-insoluble organic tail), surfactant molecules accumulate preferentially at the interface of two immiscible phases. If the concentration at the interface exceeds the critical micelle forming concentration (cmc), a colloidal surfactant solution is produced. With increasing concentration, or volume fraction of the internal phase, such a solution becomes a structured gel.

Bailey in U.S. Pat. No. 3,299,112 describes products formed from a ternary system of water, a silicone oil, and a silicone polyether. But in contrast to my invention, the products in Bailey are emulsions which are not clear; the ternary system in the '112 patent is not a gel; the silicone oil in Bailey is not a volatile cyclic VMS; and where Bailey does describe a linear silicone oil, it is not a volatile linear silicone oil.

Rather, the silicone oil in Bailey corresponds to $R''_3SiO(R''_2SiO)_xSiR''_3$ where x is 10–1,000. My corresponding volatile linear VMS have an "x" of 0–5, well below the range in Bailey. In fact, where "x" exceeds 5, products tend not to be clear.

Furthermore, emulsions as in Bailey are recognized as inherently unstable systems separating with time. In contrast, my gels are stable indefinitely. The order of addition of the components does influence their formation, and with mild mixing at room temperature (20°–25° C./68°–77° C.), that is sufficient to cause stable gels to form.

My clear gel has particular value in the personal care arena. Because of the unique volatility characteristics of the VMS component of my ternary system, it can be used alone, or blended with other cosmetic fluids to form a variety of over-the-counter personal care products.

Thus, it is useful as a carrier in antiperspirants and deodorants, since it leaves a dry feel, and does not cool the skin upon evaporation. It is lubricious and will improve the properties of skin creams, skin care lotions, moisturizers, facial treatments such as acne or wrinkle removers, personal and facial cleansers, liquid soaps, bath oils, perfumes, colognes, sachets, sunscreens, pre-shave and after-shave lotions, shaving soaps, and shaving lathers. It can be used in hair shampoos, hair conditioners, hair sprays, mousses, permanents, depilatories, and cuticle coats, to enhance gloss and drying time, and provide conditioning benefits.

In cosmetics, it will function as a leveling and spreading agent for pigments in make-ups, color cosmetics, foundations, blushes, lipsticks, lip balms, eyeliners, mascaras, oil removers, color cosmetic removers, and powders. It is also useful as a delivery system for oil and water soluble substances such as vitamins. When incorporated into sticks, other gels, lotions, aerosols, and roll-ons, my ternary composition imparts a dry, silky-smooth, pay-out.

Additionally, my clear gel exhibits a variety of advantageous and beneficial properties such as (i) clarity, (ii) the ability to combine properties of water and oil in a single homogeneous material, (iii) shelf stability, and (iv) ease of preparation; and consequently it has wide application but especially in cosmetics or antiperspirants.

A transparent gel for cosmetic or antiperspirant uses should be semi-solid materials at rest, but should thin sufficiently under moderately applied shear stress, to flow easily and smoothly when spread over the skin.

Beyond personal care, the gels have application in formulating consumer products such as ski waxes, insecticides, stain removal sticks, car waxes, tire treatments, and vinyl protectants.

BRIEF SUMMARY OF THE INVENTION

It is an object of my invention to form a clear silicone gel by simply combining (i) water; (ii) a volatile cyclic methyl siloxane or volatile linear methyl siloxane; and (iii) a silicone polyether surfactant. What I have accomplished is significant, because I discovered how to make clear silicone products without involving the use of high shear, and without the necessity of adding a separate-gelator such as stearyl alcohol, cetyl alcohol, or hydrogenated castor oil, to achieve a semi-solid state.

These and other objects of my invention will become apparent from a consideration of the detailed description.

BRIEF DESCRIPTION OF THE DRAWING

FIG. 1 is a ternary phase diagram of a system comprising water, octamethylcyclotetrasiloxane (D4), and the silicone polyether surfactant shown in Example I, at 25° C.; for determining composition ranges of gels prepared according to my invention. Gel compositions are defined by the shaded area ABCD, i.e., the gel region.

In FIG. 1, each of the corners represents 100 percent of the component labeled there. The side of the triangle directly opposite each corner represents zero percent of that component. Lines parallel to the opposite side represent increasing amounts of that component as they become closer to the corner.

For example, any line drawn from the corner of the component D4 to the opposite side represents varying the amount of D4 at a constant ratio with respect to the other two components $H_2O$ and SURFACTANT.

The composition of any point within the shaded area ABCD is determined by drawing lines parallel to each of the three sides through the point. The amount of each component is then read from the intersection of each line with the side of the triangle which corresponds to that component, i.e. the side beginning at 100 at each component's corner.

Technically, shaded area ABCD represents the $I_1$ or the cubic phase liquid crystal region. The remaining area of the triangle outside of shaded area ABCD contains other regions (not shown), such as regions of unstable emulsions, microemulsions $L_n$, lamellar phase liquid crystals $L_\alpha$, and hexagonal phase liquid crystals $H_1$.

DETAILED DESCRIPTION

My ternary composition contains water, a volatile cyclic or linear methyl siloxane, and a short-chain or low molecular weight silicone polyether. Those three components can be combined to form clear gel compositions without the addition of other materials.

Thus, the composition should be free of non-essential ingredients such as gelators; salts; co-surfactants; monohydroxy alcohols; and diols and triols such as ethylene glycol and glycerol. The elimination of such non-essential ingredients is especially beneficial and advantageous, as it obviates the need for refractive index matching, often resorted to in the past to achieve clear or transparent products.

The three components of my ternary system cannot be combined in any given order of addition to easily obtain a gel, however. Although these gels are manifestations of thermodynamically stable liquid crystal phases, their viscosity is very high, and they require unacceptably long periods of time to form spontaneously. Because they are shear thinning, they mix easily if only sufficient shear is applied to break down their gel structure. The amount of shear necessary to do this will be evident from the discussion below in connection with Example II. Thus, it is important that the oil component (i.e., the VMS) and the silicone polyether component be combined in the mixing container before addition of water to the container. The oil component and the silicone polyether component are then mixed together for a short period of time in the mixing container. The third component (i.e., water) is then added to the VMS and the silicone polyether in the mixing container, and the three components are mixed in the mixing container for another short period of time.

While heat enhances solubility, lowers surface tension, and reduces viscosity, its application is not required. Room temperature mixing is sufficient in most cases.

The oil component of my ternary composition, i.e., the volatile methyl siloxane, is a low viscosity silicone fluid corresponding to the average unit formula $(CH_3)_a SiO_{(4-a)/2}$ in which a has an average value of two to three. The fluid contains siloxane units joined by $\equiv Si-O-Si\equiv$ bonds. Representative units are monofunctional "M" units $(CH_3)_3 SiO_{1/2}$ and difunctional "D" units $(CH_3)_2 SiO_{2/2}$. The presence of trifunctional "T" units $CH_3 SiO_{3/2}$ results in the formation of branched cyclic volatile methyl siloxanes. The presence of tetrafunctional "Q" units $SiO_{4/2}$ results in the formation of branched linear volatile methyl siloxanes.

Linear VMS have the formula $(CH_3)_3 SiO\{(CH_3)_2 SiO\}_x Si(CH_3)_3$, and cyclic VMS have the formula $\{(CH_3)_2 SiO\}y$, in which x is 0–5, and y is 3–6. Preferably, the volatile methyl siloxane has a boiling point less than 250° C. and a viscosity of 0.65–5.0 centistokes ($mm^2/s$).

Some representative volatile methyl siloxanes are:

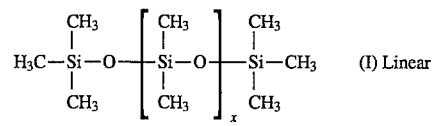
(I) Linear

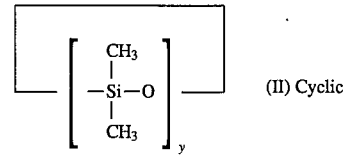
(II) Cyclic

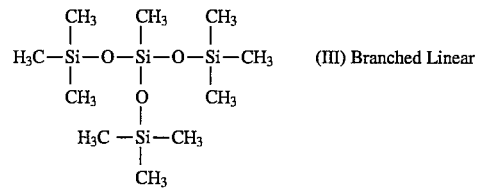
(III) Branched Linear

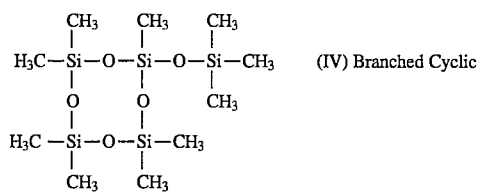
(IV) Branched Cyclic

Cyclic volatile methyl siloxanes (II) have been assigned the International Nomenclature Cosmetic Ingredient (INCI) name "CYCLOMETHICONE" by The Cosmetics, Toiletries and Fragrance Association, Inc., (CTFA) Washington, DC. Cyclic and linear methyl siloxanes are clear fluids, essentially odorless, non-toxic, non-greasy, non-stinging, and non-irritating to skin. VMS leave substantially no residue after 30 minutes at room temperature (20°–25° C./68°–77° F.) when one gram is placed at the center of No. 1 circular filter paper of 185 millimeters diameter, supported at its perimeter in open room atmosphere. Volatile methyl siloxanes may be used alone or mixed together. Mixtures result in solutions having evaporating behaviors different from individual fluids.

Representative linear volatile methyl siloxanes (I) are hexamethyldisiloxane (MM) with a boiling point of 100° C., viscosity of 0.65 mm²/s, and formula Me₃SiOSiMe₃; octamethyltrisiloxane (MDM) with a boiling point of 152° C., viscosity of 1.04 mm²/s, and formula Me₃SiOMe₂SiOSiMe₃; decamethyltetrasiloxane (MD₂M) with a boiling point of 194° C., viscosity of 1.53 mm²/s, and formula Me₃SiO(Me₂SiO)₂SiMe₃; dodecamethylpentasiloxane (MD₃M) with a boiling point of 229° C., viscosity of 2.06 mm²/s, and formula Me₃SiO(Me₂SiO)₃SiMe₃; tetradecamethylhexasiloxane (MD₄M) with a boiling point of 245° C., viscosity of 2.63 mm²/s, and formula Me₃SiO(Me₂SiO)₄SiMe₃; and hexadecamethylheptasiloxane (MDBM) with a boiling point of 270° C., viscosity of 3.24 mm²/s, and formula Me₃SiO(Me₂SiO)₅SiMe₃.

Representative cyclic volatile methyl siloxanes (II) are hexamethylcyclotrisiloxane (D₃) a solid with a boiling point of 134° C. and formula {(Me₂)SiO}₃; octamethylcyclotetrasiloxane (D₄) with a boiling point of 176° C., viscosity of 2.3 mm²/s, and formula {((Me₂)SiO}₄; decamethylcyclopentasiloxane (D₅) with a boiling point of 210° C., viscosity of 3.87 mm²/s, and formula {(Me₂)SiO}₅; and dodecamethylcyclohexasiloxane (D₆) with a boiling point of 245° C., viscosity of 6.62 mm²/s, and formula {(Me₂)SiO}₆.

Representative branched volatile methyl siloxanes (III) and (IV) are heptamethyl-3-{(trimethylsilyl)oxy}trisiloxane (M₃T) with a boiling point of 192° C., viscosity of 1.57 mm²/s, and formula C₁₀H₃₀O₃Si₄; hexamethyl-3,3,bis{(trimethylsilyl)oxy}trisiloxane (M₄Q) with a boiling point of 222° C., viscosity of 2.86 mm²/s, and formula C₁₂H₃₆O₄Si₅; and pentamethyl {(trimethylsilyl)oxy} cyclotrisiloxane (MD₃) with the formula C₈H₂₄O₄Si₄.

One preferred VMS component of my ternary system is octamethylcyclotetrasiloxane [(CH₃)₂SiO]₄. It has a viscosity of 2.3 centistokes (mm²/s) at 25° C., and is referred to as "D4" since it contains four difunctional "D" units (CH₃)₂SiO₂/₂, i.e.,

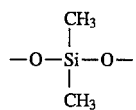

Four "D" units combine to form octamethylcyclotetrasiloxane which can be shown by either structure below:

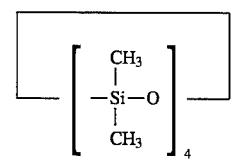

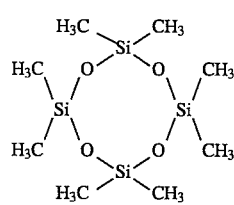

D4 often referred to as TETRAMER has a higher viscosity (2.3 mm²/s) and is thicker than water (1.0 mm²/s), yet D4 needs 94% less heat to evaporate than water.

Another preferred VMS component of my ternary system is decamethylcyclopentasiloxane (D5), often referred to as PENTAMER, and shown below:

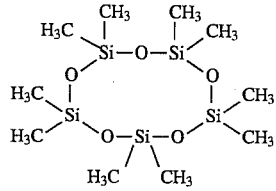

The other component of my ternary system, in addition to water and VMS, is a short-chain or low molecular weight silicone polyether. Representative linear polyethers are:

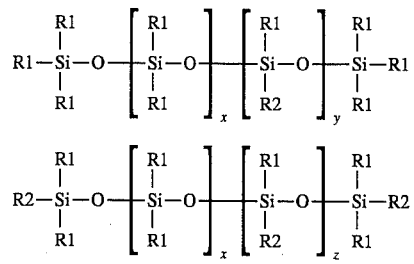

Cyclic polyethers shown below can also be used.

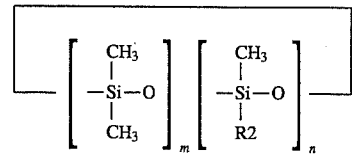

In these structures, R1 is an alkyl group containing 1–6 carbon atoms such as methyl, ethyl, propyl, butyl, pentyl, and hexyl; R2 is the radical —(CH₂)ₐO(C₂H₄O)ᵦ(C₃H₆O)ᵧR3; x is 0–3; y is 1–3; z is 0–2; m is 3–5; n is at least one; a is 3–6; b is 10–30; c is 0–5; and R3 is hydrogen, a methyl radical, or an acyl radical such as acetyl. Preferably, R1 is methyl; x is zero; y is one; z is one; n is one; b is 13–24; c is zero; and R3 is hydrogen. Most preferably, b is about 16–20.

While the compositions according to my invention may contain 5–70% by weight of surfactant, most preferably they contain about 15–30% by weight of surfactant. The remainder of the composition is the VMS oil component and water, with the proportions of VMS and water generally falling between 40:60 to 80:20.

For purposes of my invention, the criteria used to determine optical clarity is whether text can be read with the naked eye through a two centimeter diameter bottle filled with the gel.

This is a reliable and legitimate technique for evaluating gels and microemulsions. For example, as noted in the textbook *Microemulsions Theory and Practice,* Edited by Leon M. Prince, Academic Press, Inc., Pages 7–10, New York (1977), the "Visual recognition of microemulsions should not be taken lightly. In fact, the microemulsion chemist should train himself carefully in this art. Use of sunlight rather than an artificial source of light is recommended. The eye is better than a microscope because the limit of resolution of a light microscope in blue light is only about 0.1 μm so that droplets smaller than 0.14 μm cannot be seen".

The following examples show my invention in more detail.

EXAMPLE I

I formed an optically clear gel at room temperature by first adding 70 parts of octamethylcyclotetrasiloxane (D4) to a mixing bowl. I then added to the mixing bowl 45 parts of silicone polyether. These two components were mixed together in the mixing bowl for ten seconds using a single speed HAUSCHILD DENTAL MIXER. Next, I added 45 parts of de-ionized water to the mixing bowl. The three components were then mixed together in the mixing bowl for another ten seconds using the single speed HAUSCHILD DENTAL MIXER. The solution gelled and was clear. I was able to read text through a two centimeter diameter bottle filled with the gel. The silicone polyether used in this and the following examples was the trisiloxane:

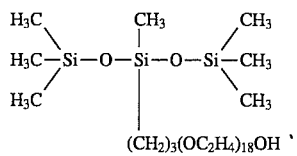

$(CH_2)_3(OC_2H_4)_{18}OH$

The viscosity and shear thinning properties were similar to those obtained in Example II.

EXAMPLE II

I repeated Example I and formed an optically clear gel at room temperature by first adding 60 parts of decamethylcyclopentasiloxane (DS) to a mixing bowl. I then added to the mixing bowl 45 parts of silicone polyether. These two components were mixed together in the mixing bowl for ten seconds using the single speed HAUSCHILD DENTAL MIXER. Next, I added 46 parts of de-ionized water to the mixing bowl. The three components were then mixed together in the mixing bowl for another ten seconds using the single speed HAUSCHILD DENTAL MIXER. The solution gelled and was clear. The optical clarity was the same as obtained in Example I.

The flow properties of the gel formed in this example were examined using a Carri-Med rheometer, in which the viscosity was determined at linearly increasing values of shear stress ranging from 0 to 17,500 dyne/cm². At a low applied shear stress of about 2,500 dyne/cm². or less, which corresponds to rest conditions, the measured viscosity was about 700,000 poise (70 million centipoise/70 million mPa.s). This value was found to fall smoothly to less than 10,000 poise (1 million centipoise/1 million mPa-s) at an applied shear stress of about 15,000 dyne/cm².

EXAMPLE III

I repeated Example I and formed an optically clear gel at room temperature by first adding 60 parts of D4 to a mixing bowl. I then added to the mixing bowl 45 parts of silicone polyether. These two components were mixed together in the mixing bowl for ten seconds using the single speed HAUSCHILD DENTAL MIXER. Next, I added 49 parts of de-ionized water to the mixing bowl. The three components were then mixed together in the mixing bowl for another ten seconds using the single speed HAUSCHILD DENTAL MIXER. The solution gelled and was clear. The optical clarity was the same as obtained in Example I. The viscosity and shear thinning properties were similar to those obtained in Example II.

The following example illustrates preparation of a gel composition according to my invention using a linear volatile methyl siloxane instead of a cyclic volatile methyl siloxane.

EXAMPLE IV

I repeated Example I and formed an optically clear gel at room temperature by first adding 60 parts of dodecamethylpentasiloxane (MDBM) to a mixing bowl. I then added to the mixing bowl 45 parts of silicone polyether. These two components were mixed together in the mixing bowl for ten seconds using the single speed HAUSCHILD DENTAL MIXER. Next, I added 52 parts of de-ionized water to the mixing bowl. The three components were then mixed together in the mixing bowl for another ten seconds using the single speed HAUSCHILD DENTAL MIXER. The solution gelled and was clear. The optical clarity was the same as obtained in Example I. The viscosity and shear thinning properties were similar to those obtained in Example II.

The following two examples illustrate preparation of clear gel antiperspirants. In Examples V and VI, an antiperspirant salt was incorporated into my clear silicone gel.

EXAMPLE V

I repeated Example I and formed an optically clear gel at room temperature by first adding 61 parts of D4 to a mixing bowl. I then added to the mixing bowl 46 parts of silicone polyether. These two components were mixed together in the mixing bowl for ten seconds using the single speed HAUSCHILD DENTAL MIXER. Next, I added 60 parts of an aqueous solution containing 10% of the antiperspirant active Aluminum Chlorohydrate (ACH) to the mixing bowl. The components were then mixed together in the mixing bowl for another ten seconds using the single speed HAUSCHILD DENTAL MIXER. The solution gelled and was clear. The optical clarity was the same as obtained in Example I. The viscosity and shear thinning properties were similar to those obtained in Example II.

EXAMPLE VI

I repeated Example I and formed an optically clear gel at room temperature by first adding 60 parts of D4 to a mixing bowl. I then added to the mixing bowl 46 parts of silicone polyether. These two components were mixed together in the mixing bowl for ten seconds using the single speed HAUSCHILD DENTAL MIXER. Next, I added 69 parts of an aqueous solution containing 20% of the antiperspirant active Aluminum Chlorohydrate to the mixing bowl. The components were then mixed together in the mixing bowl for another ten seconds using the single speed HAUSCHILD DENTAL MIXER. The solution gelled and was clear. The optical clarity was the same as obtained in Example I. The viscosity and shear thinning properties were similar to those obtained in Example II.

Other antiperspirant salts can be used in Examples V and VI such as Aluminum Dichlorohydrate, Aluminum Sesquichlorohydrate, Aluminum-Zirconium Trichlorohydrex-Gly (AZG), Aluminum-Zirconium Tetrachlorohydrex-Gly, Aluminum-Zirconium Pentachlorohydrex-Gly, and Aluminum-Zirconium Octachlorohydrex-Gly. Any formulated antiperspirant product should contain a maximum use level of antiperspirant salt active of 20% by weight AZG-type and 25% by weight ACH-type on an anhydrous basis.

Gels prepared according to Examples I–VI were semi-solid materials at rest, which shear thinned upon being subjected to moderately applied shear stress.

Other variations may be made in compounds, compositions, or methods described herein without departing from the essentials of my invention, the forms of which are exemplary and not intended as limitations on its scope defined in the claims.

I claim:

1. A method of making a gel composition comprising sequentially (i) combining 15–30% by weight of a silicone polyether based on the weight of the composition, and a cyclic methyl siloxane of the formula $\{(CH_3)_2SiO\}_p$ or a linear methyl siloxane of the formula $(CH_3)_3SiO\{(CH_3)_2SiO\}_qSi(CH_3)_3$ in which p is 3–6 and q is 0–5; (ii) mixing the silicone polyether with the cyclic or linear methyl siloxane; (iii) adding water to the mixture of silicone polyether and cyclic or linear methyl siloxane such that the methyl siloxane and water are in proportions between 40:60 to 80:20 by weight; and (iv) mixing the water, silicone polyether, and cyclic or linear methyl siloxane until a clear gel forms; the gel having a viscosity of about 700,000 poise at an applied shear stress of 2,500 dyne/cm² which decreases to less than about 10,000 poise at an applied shear stress of 15,000 dyne/cm²; the silicone polyether having a formula selected from the group consisting of

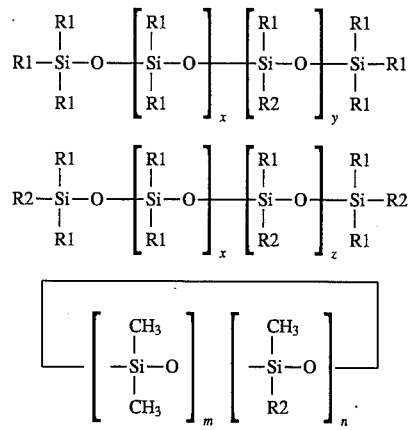

where R1 is an alkyl group containing 1–6 carbon atoms; R2 is $-(CH_2)_aO(C_2H_4O)_b(C_3H_6O)_cR3$; x is 0–3; y is 1–3; z is 0–2; m is 3–5; n is at least one; a is 3–6; b is 13–24; c is 0–5; and R3 is hydrogen, a methyl radical, or an acyl radical.

2. A method according to claim 1 in which the methyl siloxane is octamethylcyclotetrasiloxane.

3. A method according to claim 1 in which the methyl siloxane is decamethylcyclopentasiloxane.

4. A method according to claim 1 in which the silicone polyether is the compound

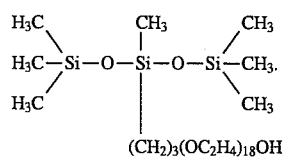

5. A gel prepared according to the method defined in claim 2, the gel having a composition defined by and within the shaded area depicted in the annexed sole FIG. 1.

6. A gel having a composition defined by and within the shaded area depicted in the annexed sole FIG. 1, the gel being prepared by a method comprising sequentially (i) combining a silicone polyether, and a cyclic methyl siloxane of the formula $\{(CH_3)_2SiO\}_p$ or a linear methyl siloxane of the formula $(CH_3)_3SiO\{(CH_3)_2SiO\}_qSi(CH_3)_3$ in which p is 3–6 and q is 0–5; (ii) mixing the silicone polyether with the cyclic or linear methyl siloxane; (iii) adding water to the mixture of silicone polyether and cyclic or linear methyl siloxane; and (iv) mixing the water, silicone polyether, and cyclic or linear methyl siloxane until a clear gel forms; the silicone polyether having a formula selected from the group consisting of

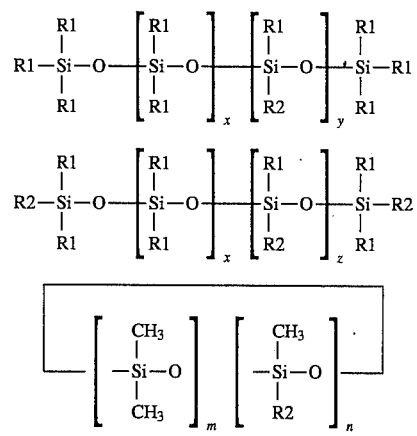

where R1 is an alkyl group containing 1–6 carbon atoms; R2 is $-(CH_2)_aO(C_2H_4O)_b(C_3H_6O)_cR3$; x is 0–3; y is 1–3; z is 0–2; m is 3–5; n is at least one; a is 3–6; b is 10–30; c is 0–5; and R3 is hydrogen, a methyl radical, or an acyl radical.

7. A gel composition containing 15–30% by weight of a silicone polyether based on the weight of the composition, the remainder of the composition being a methyl siloxane and water in proportions between 40:60 to 80:20 by weight, the composition being prepared by a method comprising sequentially (i) combining a silicone polyether and a cyclic methyl siloxane of the formula $\{(CH_3)_2SiO\}_p$ or a linear methyl siloxane of the formula $(CH_3)_3SiO\{(CH_3)_2SiO\}_qSi(CH_3)_3$ in which p is 3–6 and q is 0–5; (ii) mixing the silicone polyether with the cyclic or linear methyl siloxane; (iii) adding water to the mixture of silicone polyether and cyclic or linear methyl siloxane; and (iv) mixing the water, silicone polyether, and cyclic or linear methyl siloxane until a clear gel forms; the silicone polyether having a formula selected from the group consisting of

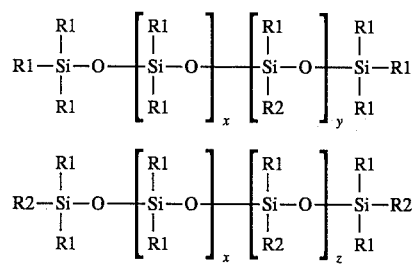

-continued
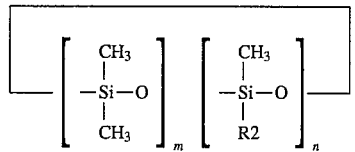
where R1 is an alkyl group containing 1–6 carbon atoms; R2 is —$(CH_2)_aO(C_2H_4O)_b(C_3H_6O)_c$R3; x is 0–3; y is 1–3; z is 0–2; m is 3–5; n is at least one; a is 3–6; b is 10–30; c is 0–5; and R3 is hydrogen, a methyl radical, or an acyl radical.
* * * * *